United States Patent
Xu et al.

(10) Patent No.: US 9,861,704 B2
(45) Date of Patent: Jan. 9, 2018

(54) POLYMERIC PRODRUG OF DISULFIRAM AND APPLICATION THEREOF

(71) Applicant: University of South Carolina, Columbia, SC (US)

(72) Inventors: Peisheng Xu, Chapin, SC (US); Huacheng He, West Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 14/962,426

(22) Filed: Dec. 8, 2015

(65) Prior Publication Data

US 2016/0166706 A1 Jun. 16, 2016

Related U.S. Application Data

(60) Provisional application No. 62/124,207, filed on Dec. 11, 2014.

(51) Int. Cl.
*A61K 47/48* (2006.01)
(52) U.S. Cl.
CPC .. *A61K 47/48176* (2013.01); *A61K 47/48215* (2013.01)
(58) Field of Classification Search
None
See application file for complete search history.

(56) References Cited

U.S. PATENT DOCUMENTS

| | | | | |
|---|---|---|---|---|
| 6,706,759 | B1* | 3/2004 | Kennedy | A61K 31/27 514/499 |
| 8,809,277 | B2 | 8/2014 | Xu et al. | |
| 9,149,535 | B2 | 10/2015 | Xu et al. | |
| 9,168,230 | B2 | 10/2015 | Xu et al. | |
| 2014/0112881 | A1* | 4/2014 | Thayumanavan | C08F 220/20 424/78.29 |
| 2015/0018308 | A1 | 1/2015 | Xu et al. | |

OTHER PUBLICATIONS

Bahadur, et al.; "Multicompartment Intracellular Self-Expanding Nanogel for Targeted Delivery of Drug Cocktail," *Advanced Materials* 2012, 24, (48), 6479-6483.

Peisheng Xu, etal; Co-pending application; U.S. Appl. No. 14/887,373; filed Oct. 20, 2015.

* cited by examiner

*Primary Examiner* — Mina Haghighatian
*Assistant Examiner* — Luke E Karpinski
(74) *Attorney, Agent, or Firm* — Dority & Manning, PA

(57) ABSTRACT

Polymer/drug conjugates that can selectively target and kill cancer cells are described. Conjugates can include a copolymer formed by the reaction of a biocompatible hydrophilic component and a disulfiram derivative. The copolymer reaction product can include additional functional groups pendant to the backbone via a disulfide linkage, for instance copper chelators. The hydrophilic component can form the polymer backbone and/or can form hydrophilic pendant groups off of the backbone. Copper ions can be associated with the copolymer.

12 Claims, 7 Drawing Sheets

POLYMERIC PRODRUG OF DISULFIRAM AND APPLICATION THEREOF

CROSS REFERENCE TO RELATED APPLICATION

The present application claims priority to U.S. Provisional Patent Application Ser. No. 62/124,207 titled "The Preparation of Polymeric Prodrug of Disulfiram and its Application" of Xu, et al. filed on Dec. 11, 2014, the disclosure of which is incorporated by reference herein.

BACKGROUND

Disulfiram (Antabuse®; 1,1',1",1'''-[disulfanediylbis(carbonothioylnitrilo)] tetraethane) when combined with metal ions has been shown to effectively kill a wide variety of cancer cells at the concentration of sub-micromolar level while not affecting normal cells. Specifically, it is believed that when disulfiram combines with metals (dithiocarbamate complexes), it can function as a proteasome inhibitor. Clinical trials have been instigated to examine effectiveness of disulfiram complexed with copper gluconate against liver cancer and of disulfiram as adjuvant against lung cancer. Unfortunately, the application of disulfiram is limited due to its extremely low bioavailability and short half-life, as well as undesirable side effects such as headache, decreased sexual ability in males, skin rash, and mood change.

To advance application of anticancer drugs, various approaches have been explored toward improvement of targeting of the anticancer drugs and decrease of side-effects. For instance, expression level difference of specific receptors on normal and cancer cells have been examined for targeting as well as unique physiological properties of tumors such as low pH, high glutathione (GSH) levels, and abnormal metal ion concentrations. Elevated copper concentration (up to 2-3 fold) has been observed in a wide spectrum of tumors including ovarian, breast, cervical, prostate, and leukemia and this has suggested targeted approaches using chelators in cancer treatment. While such approaches have provided improvement in the art, room for further improvement exists.

What are needed in the art are materials and methods that can effectively deliver active forms of disulfiram to cancer cells for effective eradication while preventing damage to healthy tissue.

SUMMARY

Objects and advantages of the invention will be set forth in part in the following description, or may be obvious from the description, or may be learned through practice of the invention.

According one embodiment, a polymer/drug conjugate is disclosed. The polymer/drug conjugate can include a biocompatible copolymer that includes a disulfiram derivative pendant to the polymer backbone via a disulfide linkage. The biocompatible copolymer also includes a hydrophilic component. The polymer/drug conjugate can be in the form of a particle, e.g., a nanoparticle, with the hydrophilic component at the exterior surface of the particle. Optionally, the polymer/drug conjugate can also include copper ions in association with the copolymer.

Also disclosed are methods for decreasing the viability of cancer cells by use of the polymer/drug conjugate. For instance, a method can include delivering the conjugate to an environment that includes cancer cells, upon which delivery the conjugate can be taken up by the cells leading to cell death.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

DETAILED DESCRIPTION

Figure 1:
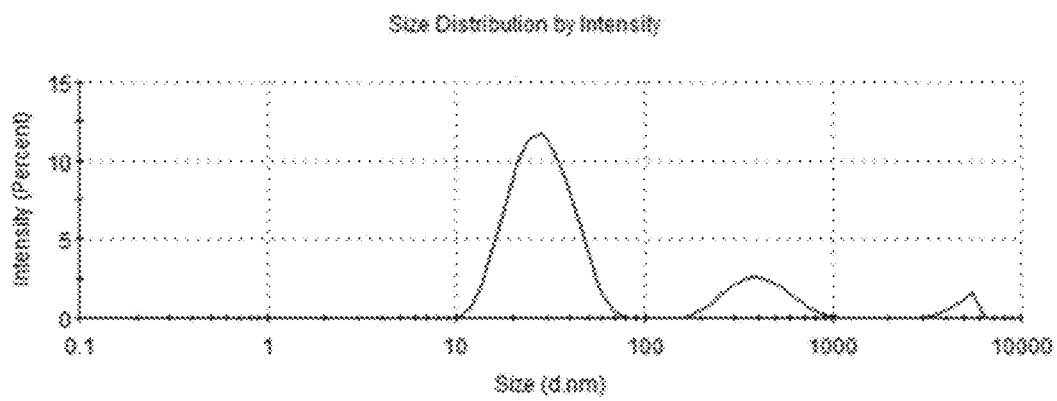
FIG. 1 presents the size distribution of nanoparticles formed of a conjugate as described herein.

Reference now will be made to the embodiments of the disclosed subject matter, one or more examples of which are set forth below. Each example is provided by way of an explanation of the subject matter, not as a limitation thereof. In fact, it will be apparent to those skilled in the art that various modifications and variations can be made without departing from the scope or spirit of the invention. For instance, features illustrated or described as one embodiment can be used on another embodiment to yield still a further embodiment. Thus, it is intended that the present disclosure cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

The "number average molecular weight" ($M_n$) is readily calculated by one of ordinary skill in the art, and generally refers to the ordinary arithmetic mean or average of the molecular weights of the individual macromolecules. It is determined by measuring the molecular weight of n polymer molecules, summing the weights, and dividing by n, such as represented in the formula:

$$\overline{M}_n = \frac{\Sigma_i N_i M_i}{\Sigma_i N_i}$$

in which $N_i$ is the number of molecules of molecular weight $M_i$.

The number average molecular weight of a polymer can be determined by gel permeation chromatography, viscometry (Mark-Houwink equation), and all colligative methods, like vapor pressure osmometry or end-group determination.

The "weight average molecular weight" ($M_w$) is readily calculated by one of ordinary skill in the art, and generally refers to:

$$\overline{M}_u = \frac{\Sigma_i N_i M_i^2}{\Sigma_i N_i M_i}$$

in which $N_i$ is the number of molecules of molecular weight $M_i$.

The weight average molecular weight can be determined by light scattering, small angle neutron scattering (SANS), X-ray scattering, and sedimentation velocity.

The polydispersity index (PDI) is a measure of the distribution of molecular mass in a given polymer sample. The PDI calculated is the weight average molecular weight divided by the number average molecular weight. It indicates the distribution of individual molecular masses in a batch of polymers. The PDI has a value equal to or greater than 1, but as the polymer chains approach uniform chain length, the PDI approaches unity (i.e., 1).

The present disclosure is generally directed to conjugate materials that can effectively target and kill cancer cells. More specifically, the materials can include a copolymer that includes a disulfiram derivative pendant to a polymeric backbone via a disulfide linkage. The copolymer also includes a hydrophilic component. The hydrophilic component can form the polymer backbone and/or can form hydrophilic pendant groups off of the backbone. The copolymer can optionally include additional pendant groups, for instance copper complexing functional groups, that can be pendant to the polymer backbone via a disulfide linkage.

Optionally, a conjugate material can include copper ions in combination with the copolymer. Copper ions can be associated with the copolymer according to any relationship. For instance, the copper ions can be associated with the copolymer via formation of a complex between a suitable reactive functionality (e.g., a pyridine functionality) and the copper ions, but the association is not limited to the formation of a complex and other associations are encompassed herein.

In one embodiment, upon formation, the copolymer can self-assemble in the form of a particle, e.g., a nanoparticle, that can be suitable for safe and effective cancer therapy with the hydrophilic component of the copolymer being at the exterior surface of the particle. The formation of the nanoparticle can endow two advantages for cancer therapy. First, due to the existence of the hydrophilic corona (e.g., polyethylene glycol), the circulation time of the copolymer, and in particular the disulfiram derivative, in the blood stream can be greatly extended. Second, by taking advantage of the leaky structure of capillaries in tumorous tissue, the formed nanoparticle can be enriched in the tumor through the so called enhanced permeability and retention (EPR) effect.

Without wishing to be bound to any particular theory, it is believed that the copolymer can target and enter cancer cells through interaction with exofacial thiols. Following cellular take-up, the disulfiram component of the side groups can be released from the polymer backbone via GSH action, leading to cell death.

Beneficially, the polymer/drug conjugates are non-toxic to non-cancer cells and as such can be utilized with little or no side effects. Due to the differences between normal and cancer cells in intracellular GSH level as well as expression level of various genes, it is believed that the disclosed materials can exhibit high selectivity in killing a broad spectrum of cancer cells, including drug resistant cancer cells, while sparing normal cells. The combination of minimal side effects, enhanced efficacy, longer half-life, exclusive selectivity for cancer cells, and wide-spectrum of anti-cancer activity can provide a successful approach to cancer therapy. For instance, the disclosed materials can be effective in treating ovarian cancer, breast cancer, cervical cancer, prostate cancer, lung cancer and leukemia, among others.

The hydrophilic component of the polymer can be based upon any biocompatible polymer or oligomer capable of directly or indirectly copolymerizing with the disulfiram monomer. By way of example and without limitation, the hydrophilic component can include one or more of polyethylene glycol, poly(N-isopropylacrylamide) (polyNIPAAm), poly(N-(2-hydroxypropyl)methacrylamide) (polyHPMA), poly(acrylic acid) (PAAc), poly(DL-lactic acid-co-glycolic acid) (PLGA), poly(L-histidine), etc.

In one embodiment, the copolymer can be formed in a two-step process. In a first step, a copolymer including a hydrophilic portion and a disulfide-containing component can be formed and following, this copolymer can be further reacted with disulfiram or a derivative thereof to form the polymer/drug conjugate.

By way of example, in a first step of a two-step formation process, a disulfide-containing monomer can be reacted with the hydrophilic component. In one particular embodiment, the hydrophilic component can be poly(ethylene glycol) methacrylate having the general structure:

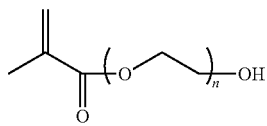

The hydrophilic component can be polymeric. For instance, polyethylene glycol methacrylate used in a formation process can include polymers in which n in the above structure is from about 4 to about 1,000, from about 5 to about 100, or from about 6 to about 20 in some embodiments.

The hydrophilic component can react with one or more disulfide-containing monomers in a first step of a formation process. For example, the disulfide-containing monomer can include a terminal acrylate for polymerization with the hydrophilic component in conjunction with a disulfide for reaction with a disulfiram derivative in a second formation step. In one embodiment, the disulfide-containing monomer can be a pyridine-2-thiol monomer and upon reaction with the hydrophilic component can form a polymer that includes pyridine-2-thiol pendant groups. Pyridine-2-thiol pendant groups can be desirable in one embodiment as upon formation of the final copolymer, a number of the pyridine-2-thiol groups can remain on the polymer and provide a site for interaction with copper ions.

By way of example, and without limitation, pyridine-2-thiol monomers as may be copolymerized with a hydrophilic component in a first step of a two-step formation process can include one or more of:

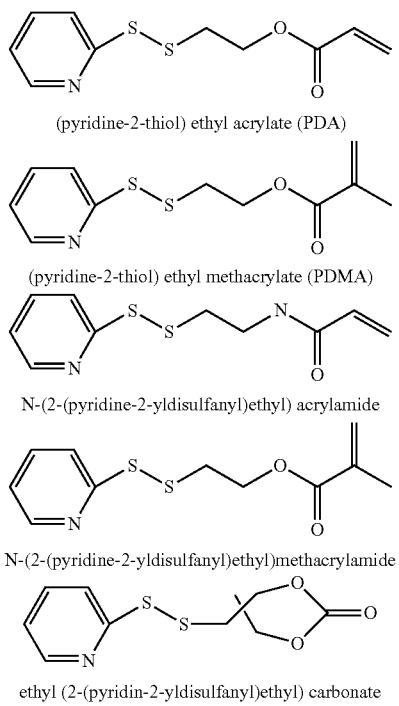

This reaction can be facilitated by any suitable catalyst. For example, the catalyst used in the reaction can be, in particular embodiments, azobisisobutyronitrile (AIBN), benzoyl peroxide, potassium persulfate, or combinations thereof. The polymerization can be free radical polymerization or living radical polymerization including stable free radical mediated polymerization (SFRP), atom transfer radical polymerization (ATRP), reversible addition-fragmentation chain transfer (RAFT) polymerization, and iodine-transfer polymerization. The last monomer of the above examples (ethyl (2-(pyridin-2-yldisulfanyl)ethyl) carbonate) can be polymerized using isopropanol as an initiator and Sn(Oct)$_2$ as a catalyst through ring-opening polymerization.

Following the polymerization reaction, a copolymer can be formed that includes disulfide containing units pendant to the backbone of the polymer. For instance, in those embodiments in which a pyridine-2-thiol monomer is polymerized with a poly(ethylene glycol)methacrylate, the resulting copolymer can include pendant groups of the pyridine-2-thiol component, e.g., (pyridine-2-thiol)ethyl acrylate groups, and pendant groups of the hydrophilic polymer, e.g., (polyethylene glycol) methacrylate groups and can have the following general structure:

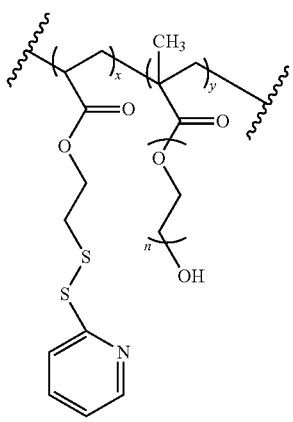

As can be seen, in this particular embodiment, the hydrophilic component of the copolymer can form pendant groups upon the polymerization reaction. In such embodiments, the molar ratio of the disulfide containing repeating units of the polymer to hydrophilic pendant repeating units of the polymer (e.g., the poly(ethylene glycol) methacrylate units) can be from about 100:1 to about 1:100 (the ratio of x to y in the above structure), for instance from about 20:1 to about 1:20 in some embodiments, from about 10:1 to about 1:10 in some embodiments, or about 1:1 in some embodiments.

It should be understood that the hydrophilic polymer that is copolymerized with the disulfide containing monomer need not necessarily form secondary pendant groups as is the case with the poly(ethylene glycol) methacrylate copolymerization process, and in some embodiments, the only pendant groups formed upon reaction of the hydrophilic component and the disulfide containing monomer can be the disulfide containing groups.

In addition, although shown as a block copolymer in the above structure, it is to be understood that this representation is simply short-hand for any type of copolymer (e.g., random, block, etc.) that includes repeating units of both the pyridine-2-thiol repeating units and repeating units of the hydrophilic polymer.

In the second step of the formation process, the copolymer can be further processed to include a disulfiram derivative.

Disulfiram has the following chemical formula:

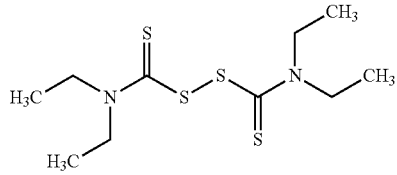

The polymer/drug conjugate can include a disulfiram derivative pendant to the polymer back bond via a disulfide linkage. In one embodiment, the polymer/drug conjugate can be formed to include an active form of disulfiram, and in one particular embodiment, the active disulfiram metabolite diethyldithiocarbamate (DDTC), which has the general structure of:

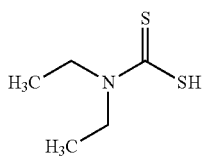

The conjugation of the disulfiram monomer with the copolymer can be carried out via a thiol-disulfide exchange reaction in which all or a portion of the disulfide containing groups can be substituted for the disulfiram component. For instance, the previously formed copolymer can be combined with DDTC in conjunction with an acid (e.g., acetic acid) at room temperature for a period of time under stirring. Following the exchange reaction, the formed copolymer can include the disulfiram component pendant to the copolymer backbone.

For example, an exemplary reaction scheme utilizing the above-described initial copolymer can be as follows:

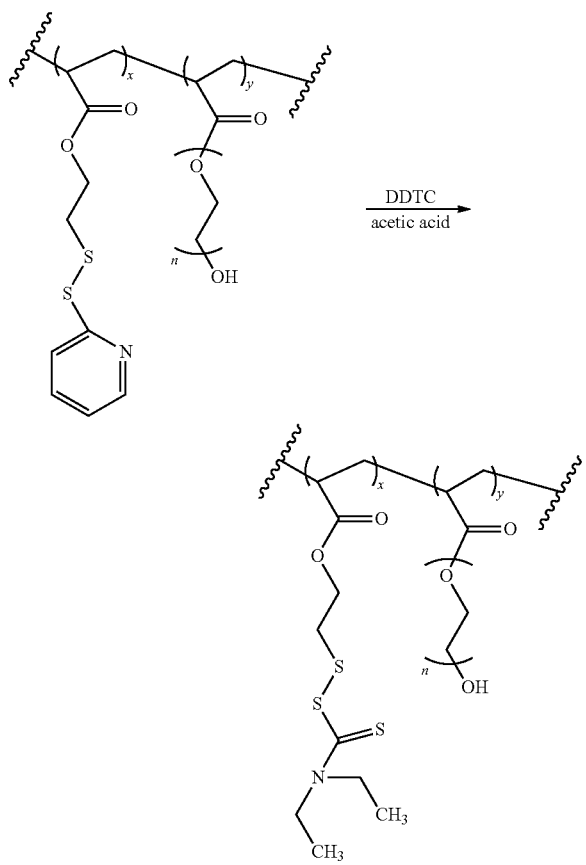

The copolymer thus formed can generally have a weight average molecular weight from about 1,000 to about 100,000, or from about 5,000 to about 35,000 in some embodiments. In one embodiment, the copolymer can have a PDI of from about 1.05 to about 3, or from about 1.15 to about 1.30 in some embodiments.

As previously mentioned, in the second step of a formation process, the disulfiram derivative need not replace all of the disulfide containing monomers of the copolymer. For instance, in one embodiment, the initial disulfide containing monomer can be a pyridine-2-thiol monomer and upon the second step of the formation process, a number of the initially formed pendant groups can remain. According to this embodiment, a reaction scheme can be as follows:

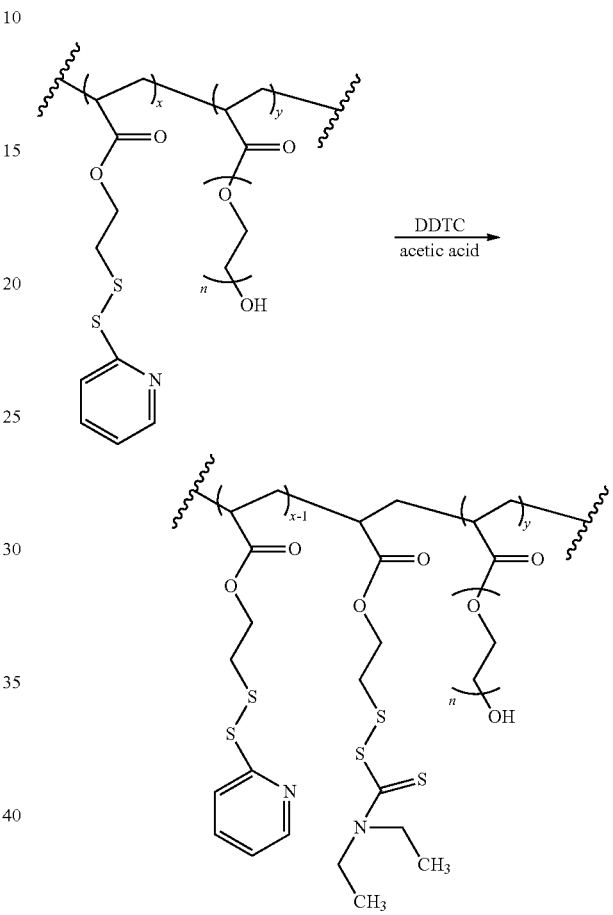

Thus, the polymer/drug conjugate can include on the copolymer the hydrophilic component, the disulfiram derivative component, and a third component that can provide a useful function, e.g., form an association with copper ions.

In one embodiment, the polymer/drug conjugate can include additional functionality. For instance, the copolymer can be formed to include one or more additional groups that can function as a chelator and form a complex with copper by thiol, amine, and/or hydroxyl, one or more of which can be included on the copolymer in addition to the disulfiram derivative and any remaining disulfide containing groups of the initial copolymer formation step. In general, additional groups can be incorporated onto the copolymer prior to addition of the disulfiram derivative, so as to prevent loss of the disulfiram groups prior to use. However, this is not a requirement of a formation process, particularly in those instances in which the chemistry utilized to incorporate additional functionality on the copolymer will not affect the existing disulfiram components of the copolymer.

By way of example, in one embodiment, a copolymer including an initial disulfide containing pendant group can be reacted with a thiol monomer that contains a carbon-bonded sulfhydryl (i.e., —C—SH or R—SH group where R represents an alkane, alkene, or other carbon-containing chain) through a thiol-disulfide exchange reaction to substitute a portion of the end groups of the initial disulfide containing monomer of the copolymer. For instance, a portion of the 2-(pyridin-2-yldisulfanyl)ethyl acrylate repeating units in a copolymer illustrated above can be converted to a modified end group. Following, the copolymer can be further reacted to include the disulfiram derivative as described above.

Any suitable thiol monomer can be utilized in a thiol-disulfide exchange reaction, including but not limited to, alkythiols having a carbon chain of about 2 to about 20 (e.g., ethanethiol, propanethiol, butanethiol, pentanethiol, etc.) generally with a functional end group opposite of the thiol group (e.g., a carboxylic group, a hydroxyl end group, an amine end group, etc.). In one embodiment, the thiol monomer can have the formula:

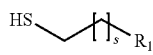

where s is 1 to 19 and $R_1$ is H, a hydroxyl group (—OH), a carboxyl group (—COOH), an aldehyde group (—CHO), an amine group (—NH$_2$), an amide group (—CONH$_2$), an amino acid, a peptide chain of at least two amino acids (e.g., arginylglycylaspartic (RGD) acid), or another organic end group.

The reaction can take place by mixing the copolymer with thiol monomer in any suitable solvent for them such as water, methanol, ethanol, dimethyl sulfoxide, methylene chloride, etc.

In one embodiment, the copolymer can be processed to include a polyhydroxy containing pendant group. By way of example, following a thiol-disulfide exchange reaction to include a functional end group on copolymer pendant groups (e.g., an amine group), the functional end groups can be further reacted with a polyhydroxy carboxylic acid to provide a polyhydroxy pendant group on the copolymer.

Polyhydroxy carboxylic acids can include cyclic or aliphatic hydroxy monocarboxylic acids of about 5 or more carbon atoms and containing about 3 or more hydroxy groups bound to adjoining carbon atoms. In one embodiment, the polyhydroxy carboxylic acids can include those obtainable by the oxidation of sugars. For example, arabonic acid, gluconic acid, galactonic acid and lactobionic acid can be utilized. Polyhydroxy carboxylic acids obtainable by other methods are also encompassed such as, and without limitation, glucoheptonic acid and mannoheptonic acid.

Through this reaction, about 1 molar % to about 50 molar % (e.g., about 5 molar % to about 25 molar %) of the original disulfide containing groups (e.g., pyridine-2-thiol groups) of the initial copolymer can be converted to modify a portion of the end groups of the copolymer. As such, the resulting modified copolymer can include the modified disulfanyl repeating units in an amount that is about 1 molar % of the original disulfide containing repeating units to about 50% of the original disulfide containing repeating units in the modified copolymer.

By way of example, upon the initial exchange reaction, a resulting modified copolymer can include 2-(pyridin-2-yldisulfanyl)ethyl acrylate repeating units, poly(ethylene glycol)methacrylate repeating units, and modified disulfanyl repeating units. In one embodiment, the modified disulfanyl repeating units can include functionality for further reaction with a polyhydroxy carboxylic acid, e.g., an amine. In this embodiment, upon the initial exchange reaction, the modified copolymer can have the following general structure:

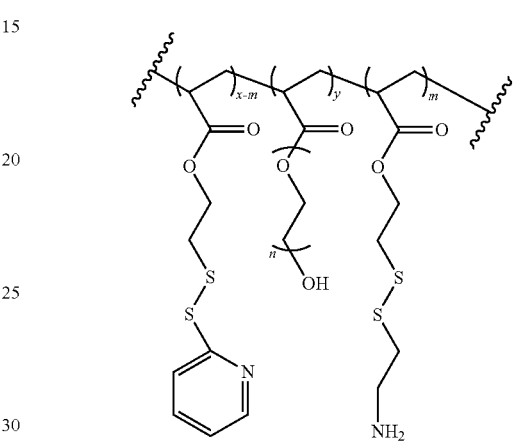

This copolymer can then be reacted with a polyhydroxy carboxylic acid, e.g., lactobionic acid, to render the copolymer having the following general structure that includes pyridine functionality in conjunction with polyhydroxy functionality:

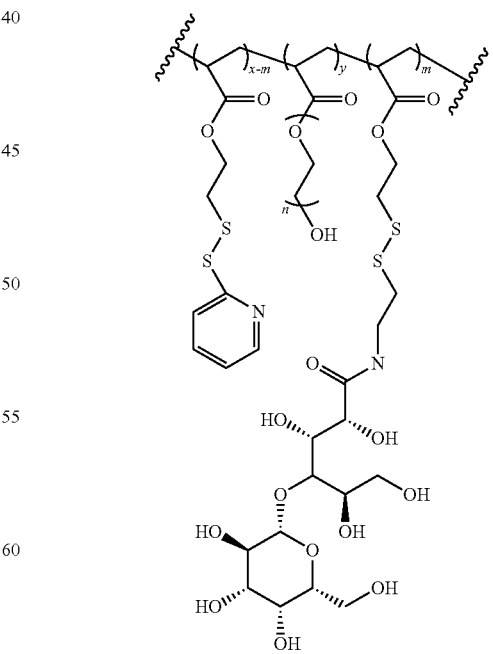

Upon further reaction with a disulfiram derivative, a copolymer can have the following structure:

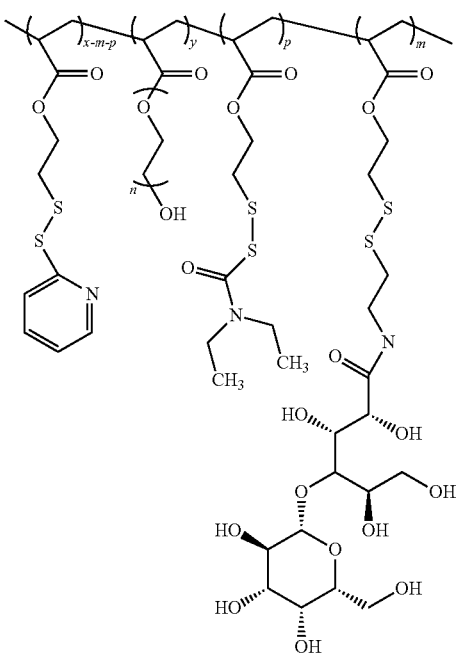

Such a polymer can have a ratio of x to y that is from about 100:1 to about 1:100 (i.e., the molar ratio of the disulfanyl monomers (total) to the backbone forming monomer that is about 100:1 to about 1:100) and of the total disulfanyl monomers, from about 1% of x to about 50% of x (i.e., about 1 molar % to about 50 molar % (e.g., about 5 molar % to about 25 molar %) can include the disulfiram derivative in conjunction with one or more additional functionalities (e.g., pyridine-2-thiol functionality and polyhydroxy functionality). Although shown as a block copolymer, it is to be understood that this representation is simply short hand for any type of copolymer (e.g., random, block, etc.) that includes repeating units as described.

Of course, additional functionality on the copolymer is not limited to polyhydroxy copper chelators. Other functional groups that can be included as pendant groups on the copolymer can include, without limitation, diethyldithiocarbamate, captopril, 6-mercaptopurine, thiorphan, dimercaprol, tiopronin, thiomandelic acid, N-acetycysteine, zofenoprilat, 2-Mercaptopyridine N-oxide, and D-penicillamine alone or in any combination.

The materials may be delivered or administered acutely or chronically according to various delivery methods, including sustained release methods, intravenous delivery, osmotic pumps, inhalation, and so forth.

Compositions for parenteral delivery, e.g., via injection, can include pharmaceutically acceptable aqueous and non-aqueous carriers, diluents, solvents or vehicles such as, without limitation, water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. In addition, the composition can contain minor amounts of auxiliary substances such as wetting or emulsifying agents, pH buffering agents and the like that can enhance the effectiveness of the biologically active compound. These compositions may also contain adjuvants such as preservatives, wetting agents, emulsifying agents and dispersing agents.

Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like.

A composition can include one or more oil-soluble antioxidants including, without limitation, butylated hydroxytoluene (BHT), ascorbyl palmitate, butylated hydroxyanisole (BHA), α-tocopherol, phenyl-a-naphthylamine, hydroquinone, propyl gallate, nordihydroguiaretic acid, and mixtures thereof as well as any other known oil-soluble antioxidant compatible with the other components of the compositions. Mineral oils, animal oils, vegetable oils and silicones can be incorporated in a topical creams or lotions as disclosed herein. In addition to such oils, other emollients and surface active agents can be incorporated in an emulsion.

Thickeners such as natural gums and synthetic polymers, as well as preservatives such as methylparaben, butyl paraben, propylparaben and phenyoxyethanol, can be included. Other active ingredients such as sunscreen materials and antimicrobial materials may be utilized in a composition, provided, of course, that they are physically and chemically compatible with the other components of the composition.

A composition may also contain, as optional additions, one or more soluble or dispersible pharmaceutically acceptable ingredients generally used in pharmaceutical emulsion compositions. Typical such ingredients include, for example, a preservative or antioxidant such as methyl or propyl paraben, butylated hydroxyanisole, imidazolidinyl urea and the like; a water or oil soluble vitamin such as vitamin C, tocopheryl linoleate and the like; and/or a colorant, odorant, humectant, thickener and the like. In general, from about 0.1 to about 15 percent total weight of such optional additives may be incorporated into a composition, depending upon the solubility or miscibility characteristic of the particular additive, it can be incorporated into whichever emulsion phase is most suitable.

A composition may be made into a wide variety of product forms suitable for, e.g., topical administration onto the skin of a subject or internal administration to the lungs, digestive tract, or vasculature. Non-limiting examples for topical administration include a lotion, an ointment, a gel, a cream, a stick, a spray, an aerosol, foam, a paste, etc.

Each additive of a composition may generally constitute between about 0.05% to about 15% of the total weight of the formulation. In one embodiment, a composition can include an additive in an amount between about 0.05% and about 10% or between about 0.05% and about 8%, or between about 0.05% and about 7%, or between about 0.05% and about 6%, or between about 0.05% and about 5% of the total weight of the formulation.

According to one embodiment, the delivery agents can be delivered in the form of an aerosol spray, from a pressurized pack or a nebulizer, for lung applications, for instance in treatment of a cancer in which the lung is affected. Additional formulations for administration may be made in accordance with methods and amounts known in the art.

The present disclosure may be better understood with reference to the examples, set forth below.

Example 1

Synthesis of LBA-PDA-PEG-DDTC and PDA-PEG-DDTC

PDA-PEG polymer was synthesized according to methods as are known in the art. Briefly, 2-(pyridin-2-yldisulfanyl)ethyl acrylate (PDA, 241.3 mg, 1 mmol) and poly(ethylene glycol) methacrylate ($PEG_{360}$, Mn=360 Da, 360 mg, 1 mmol) were dissolved in 10 mL degassed anisole. 2,2-Azobisisobutyronitrile (AIBN, 14 mg, 0.085 mmol) in 1 mL degassed anisole was then added, and the reaction mixture was stirred for 24 h at 65° C. The final product was precipitated (3×) in ice cold ether and dried for 48 h in vacuum.

To yield PDA-PEG-DDTC, PDA-PEG was modified with DDTC as shown in Scheme 1, below. Briefly, PDA-PEG (20 mg in 500 μL DMSO) was firstly mixed with DDTC (2.76 mg in 100 μL DMSO) with the addition of 10 μL acetic acid. The reaction mixture was kept at room temperature for 12 h under stirring. The resulting solution was dialyzed towards DMSO (MWCO=1,000 Da) to remove unreacted DDTC and then precipitated in cold ether and dried in a vacuum oven to obtain the PDA-PEG-DDTC. The structure of PDA-PEG-DDTC was confirmed by $^1$H-NMR.

To yield LBA-PDA-PEG-DDTC, PDA-PEG was reacted with cysteamine, lactobionic acid (LBA), and DDTC sequentially as shown in Scheme 2, below. Briefly, PDA-PEG (20 mg in 500 μL DMSO) was mixed with cysteamine (0.56 mg in 500 μL DMSO, 20% PDA function group) and reacted overnight at room temperature. Then LBA (4.33 mg in 100 μL DMSO) was activated by 1-Ethyl-3-[3-dimethylaminopropyl] carbodiimide hydrochloride (EDC, 4.64 mg in 100 μL DMSO) and N-hydroxysuccinimide (NHS) (2.79 mg in 100 μL DMSO) for 30 min and added to the polymer solution. After overnight reaction at room temperature, DDTC (2.76 mg in 100 μL DMSO) was added with 10 μL acetic acid and left for another 12 h. The final solution was dialyzed towards DMSO (MWCO=1,000 Da) to remove unreacted LBA and DDTC and then precipitated in cold ether and dried in a vacuum oven to obtain the LBA-PDA-PEG-DDTC. The structure of LBA-PDA-PEG-DDTC was confirmed by $^1$H-NMR.

$Cu^{2+}$ was incorporated with the polymer through combination with $CuCl_2$ (10 μM). FIG. 1 presents the size distribution profile of PDA-PEG-DDTC/copper nanoparticles thus formed.

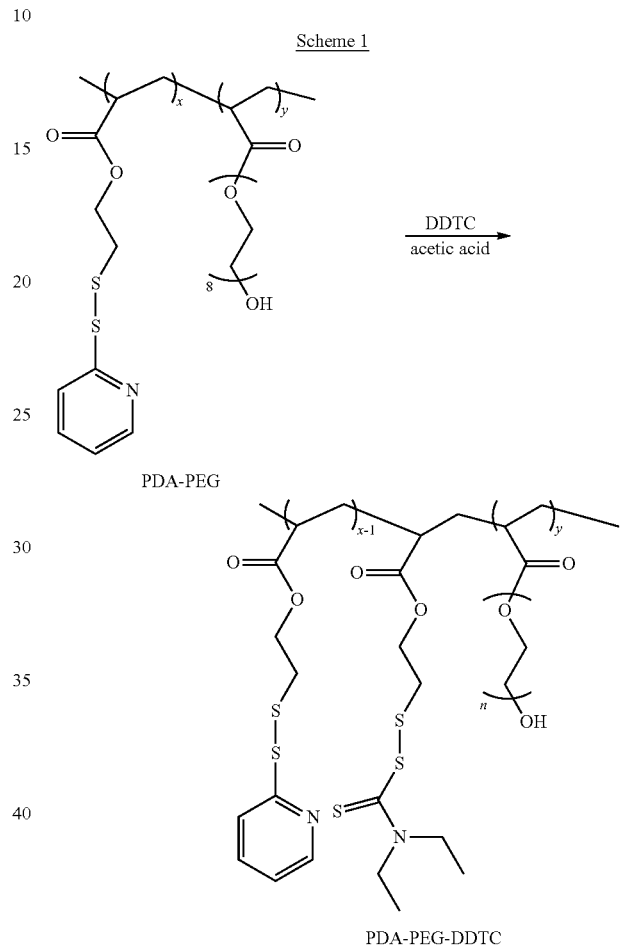

Scheme 1

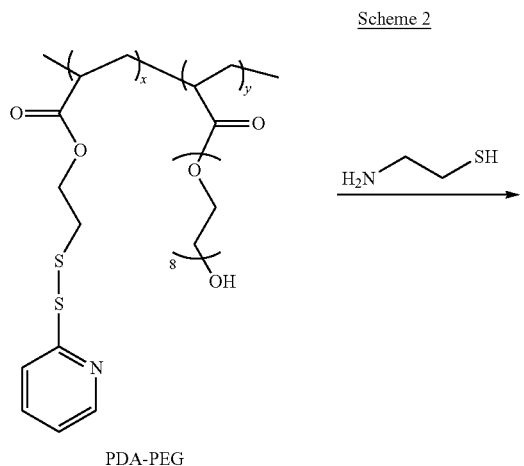

Scheme 2

-continued
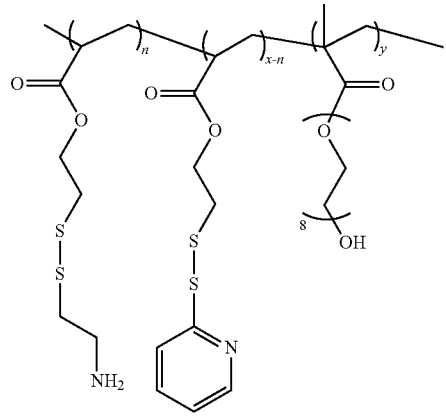
PDA-PEG-NH2
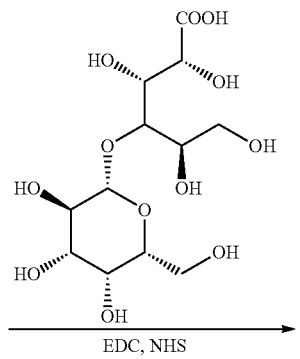
EDC, NHS
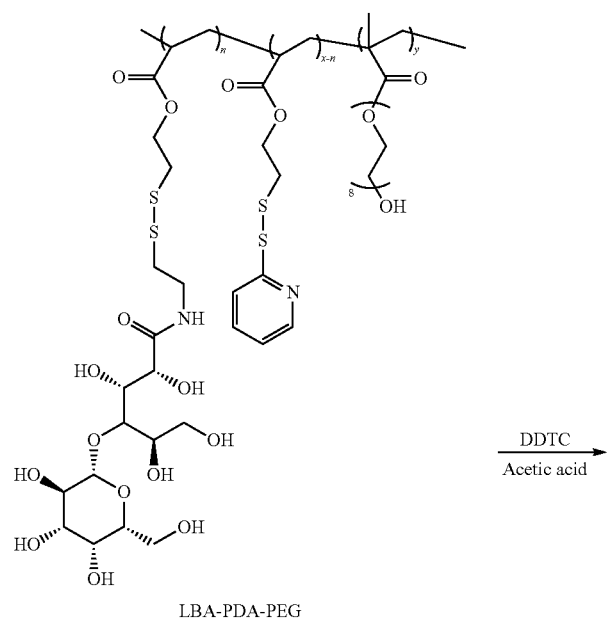
LBA-PDA-PEG
DDTC
Acetic acid

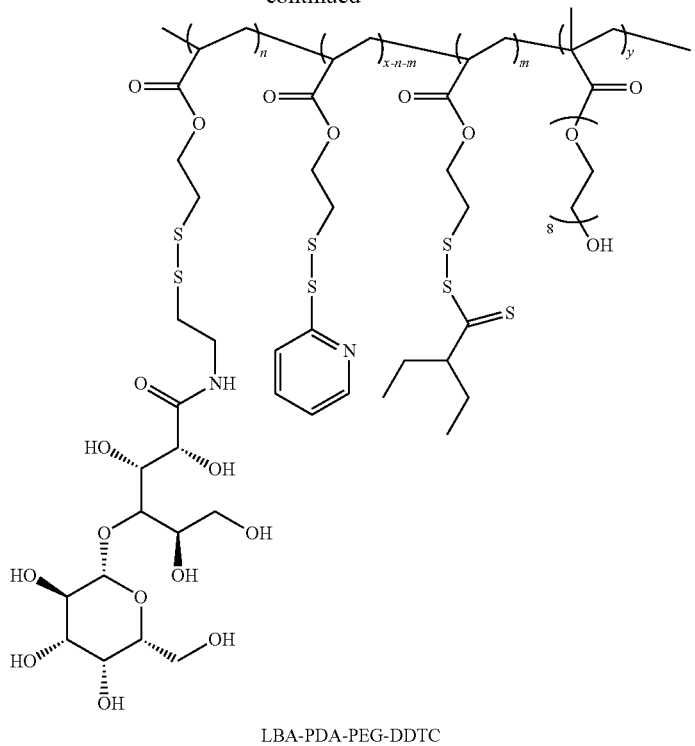

LBA-PDA-PEG-DDTC

DDTC Concentration Quantification

DDTC concentration in the polymers was quantified by HPLC. Briefly, PDA-PEG-DDTC or LBA-PDA-PEG-DDTC was firstly dissolved in ddH$_2$O (0.5 mg/mL). 100 mM TCEP was then added and incubated for 1 h to release DDTC from the polymer. Sodium bicarbonate buffer (100 mM, pH8.5) was then added to get the final polymer concentration at 0.25 mg/mL. Sodium bicarbonate was used to stabilize DDTC after its cleavage from the polymer. DDTC concentration was finally quantified by HPLC (methanol:H$_2$O (0.1% formic acid)=65:35 at 214 nm, flow rate=0.6 mL/min).

Synthesis of Cy3 Labeled PDA PEG-DDTC and LBA-PDA-PEG-DDTC

PDA-PEG was modified by Cy3 for cellular uptake study. Briefly, cysteamine (0.84 mg, 30% PDA function group) in 500 μL DMSO was added dropwise into 20 mg PDA-PEG in 500 μL DSMO and the reaction mixture was left at room temperature overnight. After overnight reaction, Cy3 NHS ester (0.142 mg in 20 μL DMSO, 5% PDA functional group) was added and the mixture was kept for reaction for 2 h at room temperature. Following, Cy3 labeled PDA-PEG-DDTC and LBA-PDA-PEG were synthesized as described above. The concentration of Cy3 in the final product was measured by microplate reader (Beckman Coulter DTX 880 Multimode Detector, Beckman Coulter, Inc).

DDTC Release from PDA-PEG-DDTC

Figure 2:
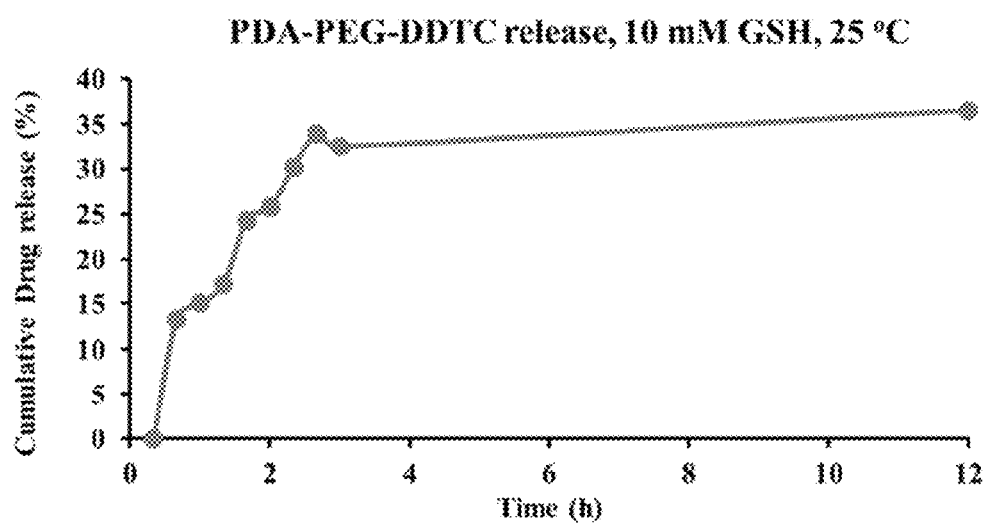
FIG. 2 illustrates the release profile over time for a disulfiram derivative from a conjugate as described herein in the presence of 10 mM glutathione (GSH).

PDA-PEG-DDTC (0.25 mg/mL) was dissolved in PBS buffer (pH7.4, 10 mM) with or without 10 mM GSH and immediately loaded to HPLC and injected every 20 min. DDTC released from polymer was then calculated referred to the calibration curve. The results are shown in FIG. 2.

Confocal Microscopy

Figure 3:
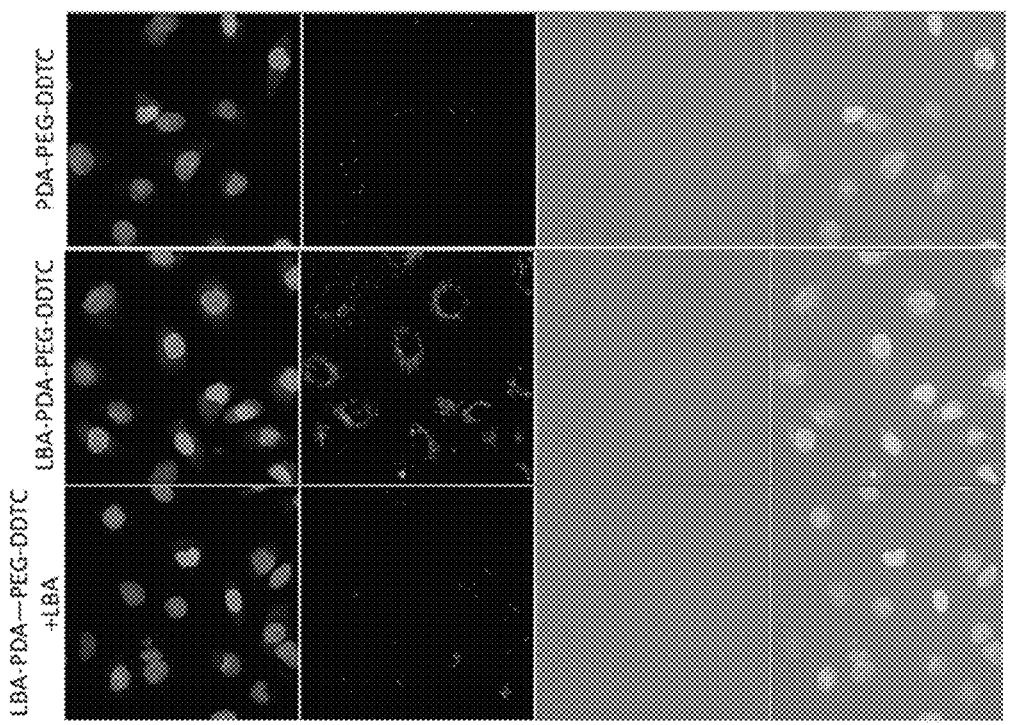
FIG. 3 includes confocal images showing the cellular uptake of conjugates as described herein by SKOV-3 cells.
Figure 4:
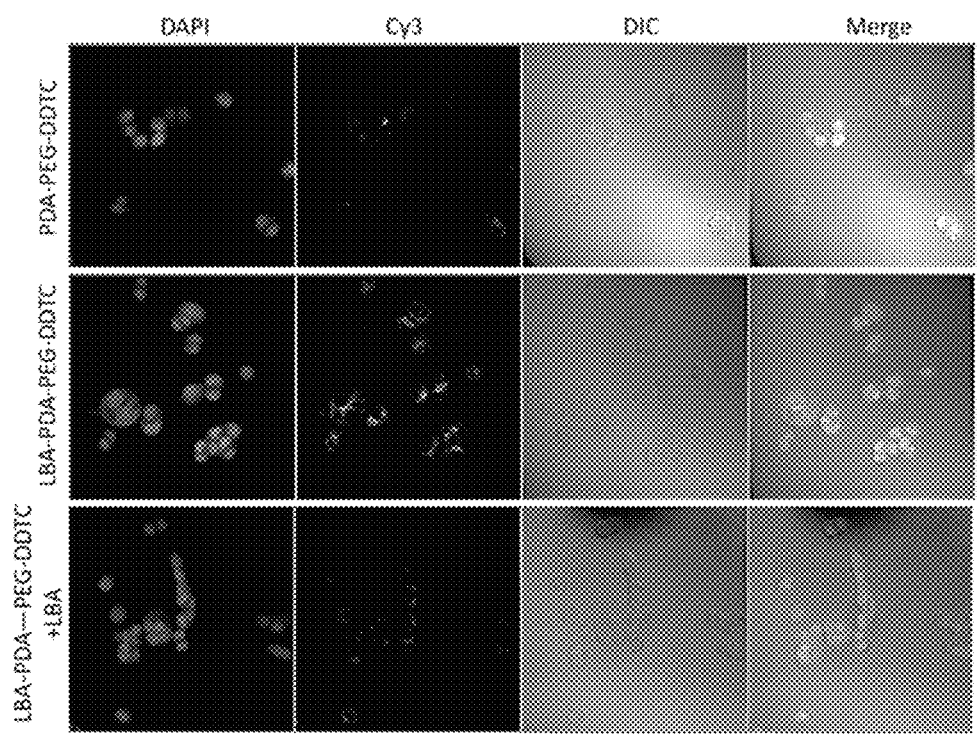
FIG. 4 includes confocal images showing the cellular uptake of conjugates as described herein by HICT-116 cells.

SKOV-3 and HCT116 (200,000 cells/dish) were seeded in 35 mm$^2$ Petri dishes (Mat Tek, MA, USA) overnight. PDA-PEG-Cy3-DDTC and LBA-PDA-PEG-Cy3-DDTC diluted in culture medium supplemented with 10 μM CuCl$_2$ were then added (equivalent to 0.1 μg/mL Cy3). To block the asialoglycoprotein receptor (ASGP-R), free LBA (1 mg/mL) was added to the dishes with LBA-PDA-PEG-Cy3-DDTC. After 3 h incubation under a humidified atmosphere of 95/5% air/CO$_2$, cells were washed by PBS (3×), fixed with formaldehyde (4.5% in PBS) and stained with Hoechst 33342 (final concentration 1 μg/mL). Then cells were analyzed under a confocal microscope (LSM 700, Carl-Zeiss Inc.). FIG. 3 presents images showing the cellular uptake of the different materials by SCOV-3 cells and FIG. 4 presents images showing uptake of the different materials by HCT-116 cells.

Flow Cytometry

Figure 5:
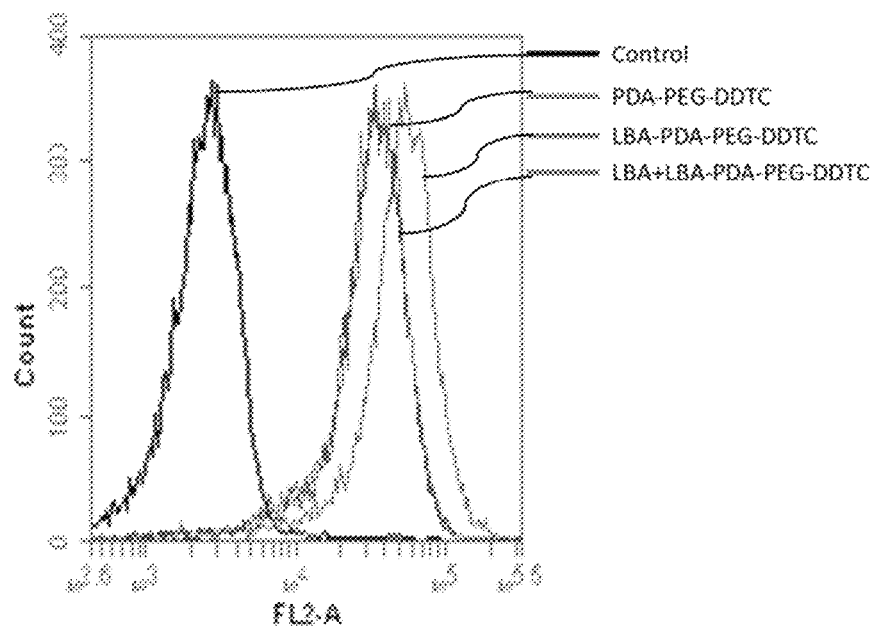
FIG. 5 presents flow cytometry spectra of uptake by SKOV-3 cells for various conjugates as described herein.
Figure 6:
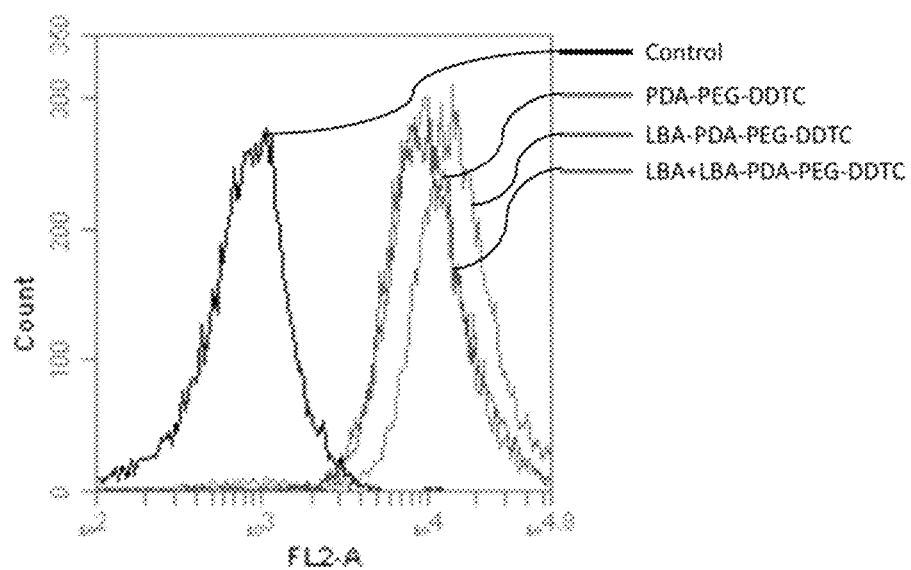
FIG. 6 presents flow cytometry spectra of uptake by HCT-116 cells for various conjugates as described herein.
Figure 7:
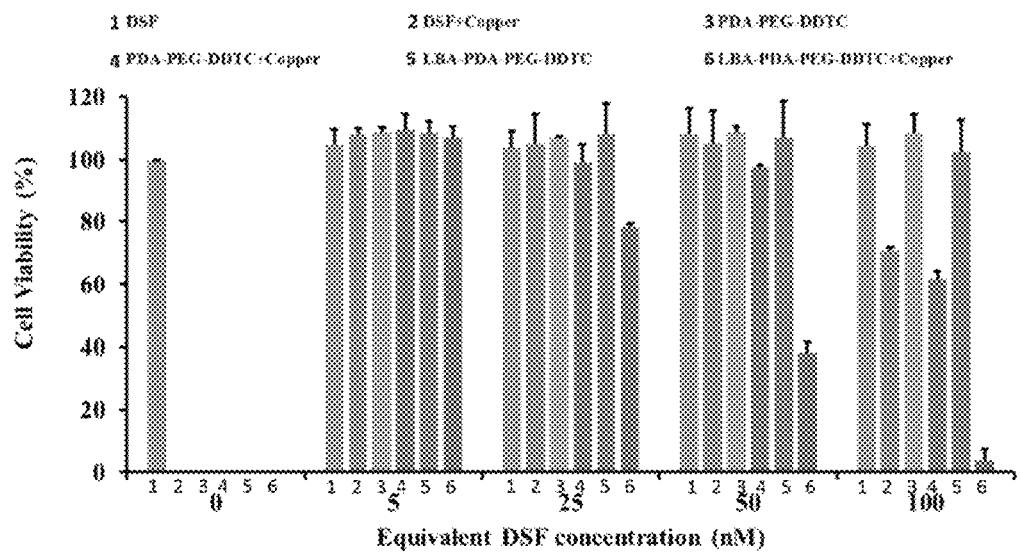
FIG. 7 illustrates the cytotoxicity of a conjugate as described herein for HCT-116 cells following 24 hr. incubation.
Figure 8:
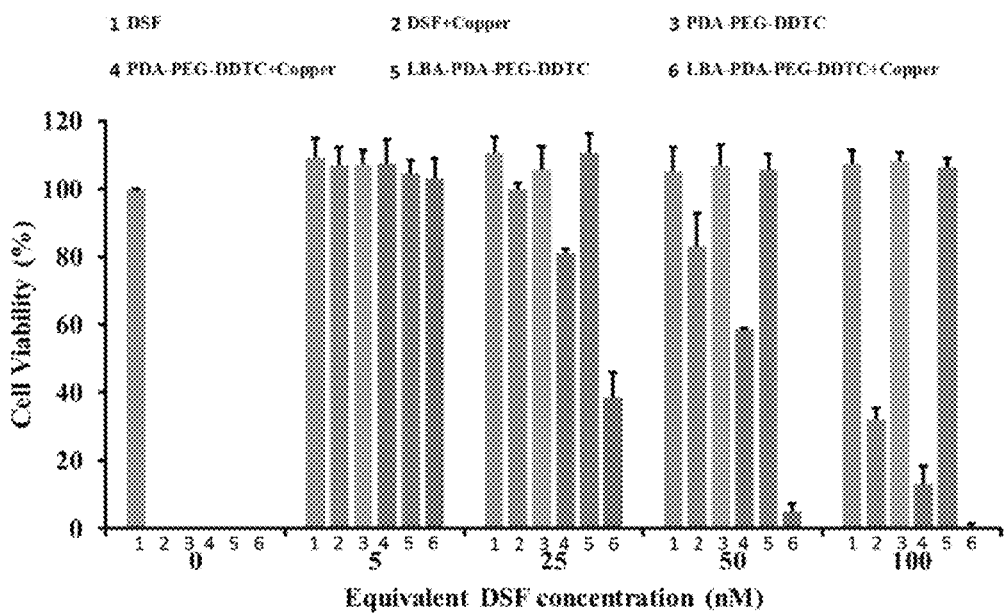
FIG. 8 illustrates the cytotoxicity of a conjugate as described herein for MDA-MB-231 cells following 24 hr. incubation.
Figure 9:
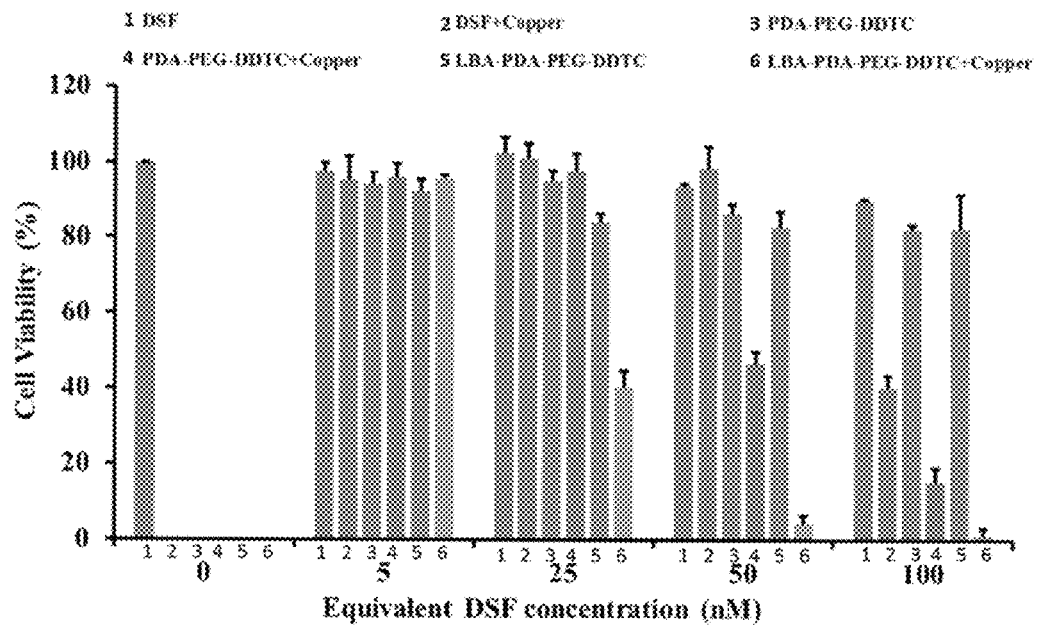
FIG. 9 illustrates the cytotoxicity of a conjugate as described herein for HKc/DR cells following 24 hr. incubation.
Figure 10:
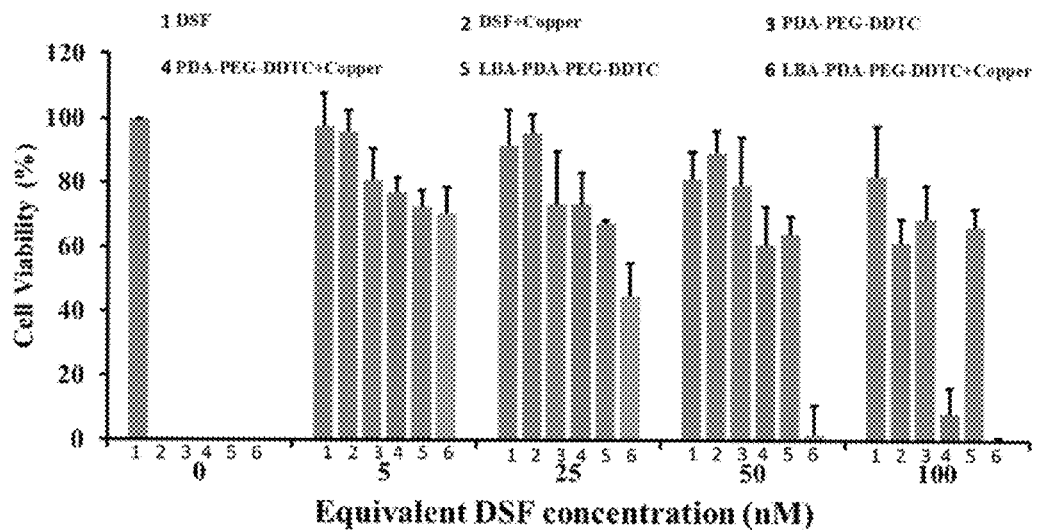
FIG. 10 illustrates the cytotoxicity of a conjugate as described herein for HKc/DR-Six1 cells following 24 hr. incubation.

SKOV-3 and HCT-116 cell (300,000 cells/dish) were seeded in 6-well plate overnight. PDA-PEG-Cy3-DDTC, LBA-PDA-PEG-Cy3-DDTC and LBA-PDA-PEG-Cy3-DDTC with free LBA (1 mg/mL) were added and incubated for 3 h at the presence of 10 μM CuCl$_2$ in medium. Then cells were washed, trypsinized, and resuspended in PBS. Cy3 positive cell population was quantified at $\lambda_{ex}$488 and $\lambda_{em}$585 nm using flow cytometry (BD Accuri C6, BD Biosciences). Flow cytometry data for the different conjugate materials and the control are shown in FIG. 5 (SKOV-3 cells) and FIG. 6 (HCT-116 cells).

MTT Assay

In vitro cytotoxicity of LBA-PDA-PEG-DDTC was evaluated in HepG2, HKc/DR, HKc/DR-Six1, MDA-MB-231 and HCT116 cell lines. Cells were seeded in 96-well plate (20,000 cells/well) for 24 prior to the study. Then a serial of concentrations of disulfiram (DSF), PDA-PEG-DDTC, LBA-PDA-PEG-DDTC in culture medium was added, supplementing with or without CuCl$_2$ (10 μM). The cells were then incubated 24 or 48 h in in 95/5% air/CO$_2$ at 37° C. MTT reagent (100 μL, 10% (w/w) in medium) was added and incubated for 4 h, following the addition of MTT stop solution. The optical density of the medium was quantified using a microplate reader (ELX808, Bio-Tech Instrument, Inc) at λ=595 nm.

Figure 11:
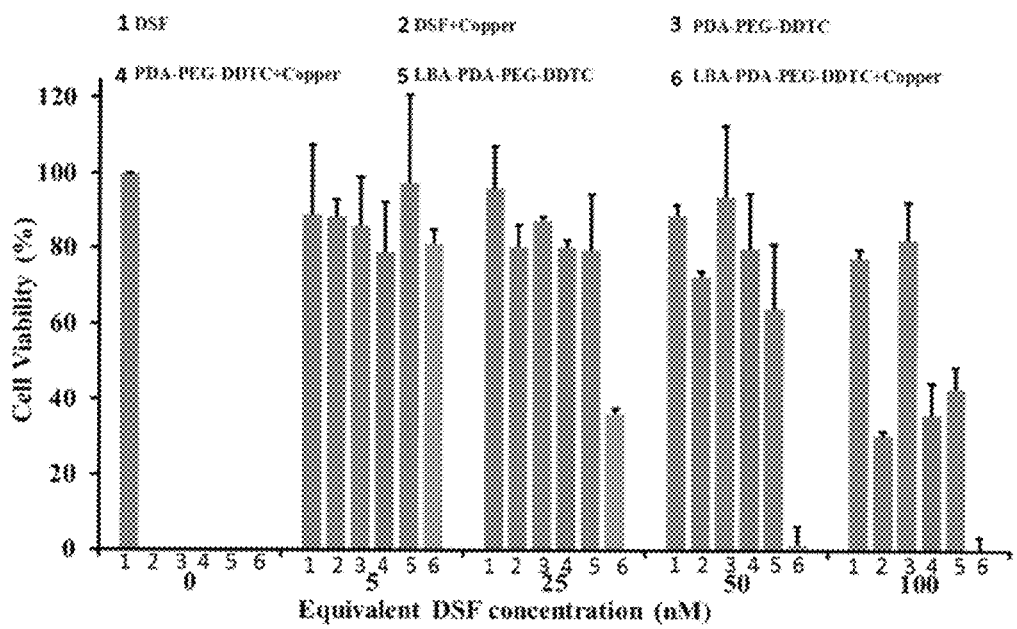
FIG. 11 illustrates the cytotoxicity of a conjugate as described herein for Hep G2 cells following 48 hr. incubation.

Cytotoxicity results are presented graphically for different disulfiram concentrations for the various cell types in FIG. 7-FIG. 11 including HCT-116 cells (FIG. 7), MDA-MB-231 cells (FIG. 8), HKc/DR cells (FIG. 9), HKc/DR-Six1 cells (FIG. 10), and Hep G2 cells (FIG. 11).

In Vivo Animal Model

Orthotopic intraperitoneal (IP) tumor mouse model was employed for the following study. In brief, luciferase-expressing SKOV-3 cells (SKOV-3 luc) were suspended in culture medium at the density of $1 \times 10^6$ cells/200 μL. Cell suspension 200 μL was injected intraperitoneally to a female nude mouse (8-10 week old, ~20 g, Jackson Laboratories). The weight of mice and the tumor burdens were monitored on an IVIS Lumina II whole body imaging system every week. Before the imaging, mice were anesthetized by 2% isoflurane, and 100 μL 30 mg/mL D-luciferin was injected intraperitoneally into the tumor-bearing mice. The whole body imaging time was optimized and all mice were imaged using identical system setting. All images were finally processed and the intensity of bioluminescence signal (expressed in radiance) from SKOV3-luc tumors was quantified by Living Image® software.

Tumor Growth Inhibitory Experiment

Two weeks after the inoculation of the cancer cells, mice were randomly assigned into five groups (n=3) and were given the following five treatments: PBS, DSF/Cu, PDA-PEG-DDTC/Cu, LBA-PDA-PEG-DDTC, and LBA-PDA-PEG-DDTC/Cu.

Figure 12:
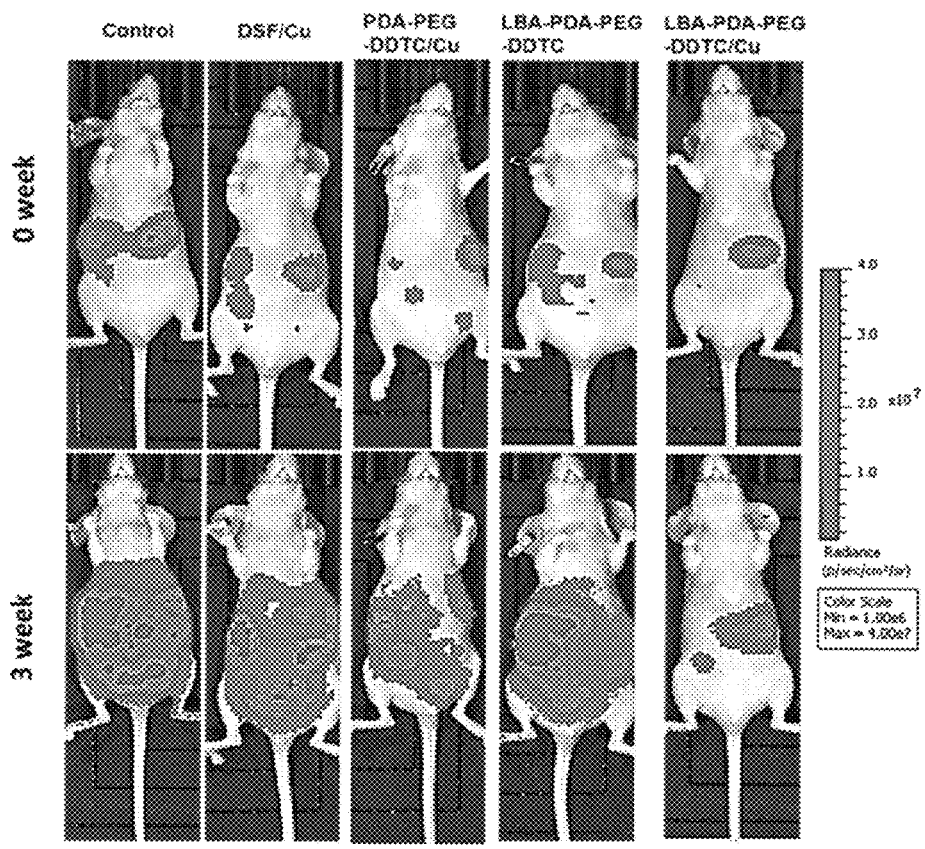
FIG. 12 presents luminescent images of mice before and after receiving different forms of disulfiram treatment over 3 weeks.
Figure 13:
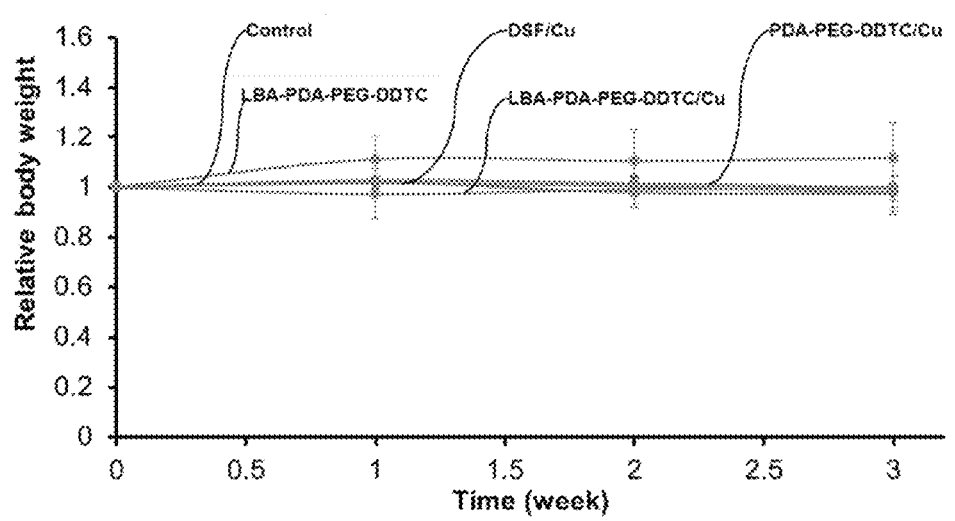
FIG. 13 illustrates mice body weight after receiving different forms of disulfiram treatment over 3 weeks.

For DSF/Cu treatment, DSF was first dissolved in corn oil and injected intraperitoneally. For other treatments, polymer and copper gluconate were first dissolved in PBS respectively, and then mixed just before injection. The final injection volume for all treatments was 250 μL and the equivalent dose for DSF was set as 5 mg/kg and 0.5 mg/kg for copper gluconate. Mice were given the treatments once per week for 3 weeks. Images are shown in FIG. 12 of mice at initiation and at week 3 for the various different DSF treatment applications and the control. FIG. 13 illustrates the change in body weight of the mice over the three week course of treatment.

Figure 14:
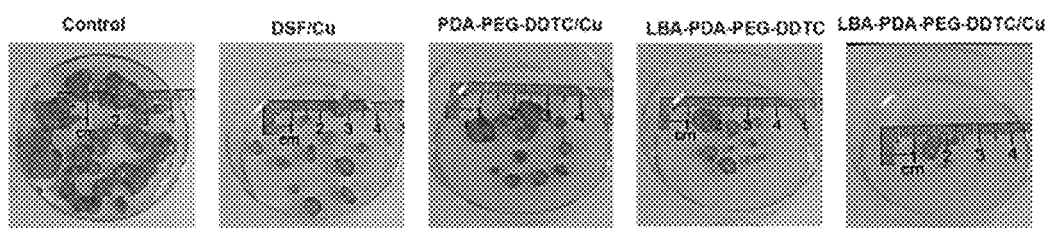
FIG. 14 illustrates ovarian tumors dissected from the orthotopic ovarian tumor model following different forms of disulfiram treatment over 3 weeks.

After three weeks of treatment, all mice were sacrificed and the blood, organs and tumors were harvested for further analysis. FIG. 14 presents images of ovarian tumors dissected from the orthotopic ovarian tumor model following the different treatment regimens as described.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A polymer/drug conjugate comprising a biocompatible copolymer, the biocompatible copolymer including diethyldithiocarbamate pendant to a backbone of the copolymer via a disulfide linkage, the biocompatible copolymer comprising a hydrophilic component, the biocompatible copolymer comprising the reaction product of an acrylamide or acrylate-containing first reactant that includes the hydrophilic component and an acrylamide or acrylate-containing second reactant, the diethyldithiocarbamate being bonded to the copolymer via the second reactant.

2. The polymer/drug conjugate of claim 1, wherein the polymer/drug conjugate is in the form of a particle, the hydrophilic component of the copolymer being primarily on an exterior surface of the particle.

3. The polymer/drug conjugate of claim 1, wherein the first reactant comprises one or more of poly(ethylene glycol) methacrylate, poly(N-isopropylacrylamide), poly(N-(2-hydroxypropyl)methacrylamide), poly(acrylic acid), poly(DL-lactic acid-co-glycolic acid), or poly(L-histidine).

4. The polymer/drug conjugate of claim 3, wherein the hydrophilic component comprises poly(ethylene glycol) groups pendant to the backbone of the copolymer.

5. The polymer/drug conjugate of claim 1, further comprising pyridine-2-thiol groups pendant to the backbone of the copolymer.

6. The polymer/drug conjugate of claim 1, wherein the second reactant comprises (pyridine-2-thiol)ethyl acrylate; (pyridine-2-thiol) ethyl methacrylate, ethyl (2-(pyridin-2-yldisulfanyl)ethyl) carbonate, N-(2-(pyridin-2-yldisulfanyl) ethyl) methacrylamide, or N-(2-(pyridin-2-yldisulfanyl) ethyl) acrylamide.

7. The polymer/drug conjugate of claim 1, further comprising copper ions.

8. The polymer/drug conjugate of claim 1, the copolymer further comprising a copper chelator on the backbone, wherein the copper chelator comprises diethyldithiocarbamate, captopril, 6-mercaptopurine, thiorphan, dimercaprol, tiopronin, thiomandelic acid, N-acetycysteine, zofenoprilat, 2-Mercaptopyridine N-oxide, and D-penicillamine alone or their combination.

9. The polymer/drug conjugate of claim 7, the biocompatible copolymer further comprising a chelating group that comprises a pyridine group, wherein the copper ions are complexed with the biocompatible polymer via the chelating group.

10. A composition configured for administration to a subject comprising the polymer/drug conjugate of claim 1.

11. A method for decreasing the viability of cancer cells, the method comprising delivering the polymer/drug conjugate of claim 1 to an environment comprising the cancer cells.

12. The method of claim 11, wherein the cancer cells comprise ovarian cancer cells, breast cancer cells, cervical cancer cells, prostate cancer cells, lung cancer cells or white blood cells.

* * * * *